United States Patent [19]

Shih et al.

[11] Patent Number: 5,171,682
[45] Date of Patent: Dec. 15, 1992

[54] **PURIFIED *BACILLUS LICHENIFORMIS* PWD-1 KERATINASE**

[75] Inventors: Jason C. H. Shih; C. Michael Williams, both of Cary, N.C.

[73] Assignee: North Carolina State University, Raleigh, N.C.

[21] Appl. No.: 769,553

[22] Filed: Oct. 1, 1991

Related U.S. Application Data

[63] Continuation-in-part of Ser. No. 581,681, Sep. 13, 1990, Pat. No. 5,063,161, which is a continuation of Ser. No. 175,476, Mar. 31, 1988, Pat. No. 4,959,311.

[51] Int. Cl.$^5$ .................. C12N 9/52; C12N 9/54; C12N 9/56
[52] U.S. Cl. .................... 435/222; 435/220; 435/221
[58] Field of Search ............... 435/220, 221, 222

[56] References Cited

U.S. PATENT DOCUMENTS

| | | | |
|---|---|---|---|
| 3,985,686 | 10/1976 | Barrat | 252/547 |
| 4,266,031 | 5/1981 | Tang et al. | 435/188 |
| 4,908,220 | 3/1990 | Shih et al. | 426/61 |
| 4,927,558 | 5/1990 | Asslyng et al. | 252/174.12 |
| 4,959,311 | 9/1990 | Shih et al. | 435/68 |

OTHER PUBLICATIONS van der Laan et al., *Applied and Environmental Microbiology*, 57, No. 4, 901-909, (1991).
Williams et al., *Applied and Environmental Microbiology*, 56, No. 6, 1509-1515 (1991).
Williams et al., *Poultry Science*, 70, 85-94 (1991).
Adler-Nissen, Enzymic Hydrolysis of Food Proteins, preface, contents, 20-21, 99-100, 368, 372, 373, 374, 377, 387-388, 402 (1986).
Rufo et al., *Journal of Bacteriology*, 172, No. 2, 1019-1023 (1990).
Williams et al., *J. Appl. Bacteriol.*, 67, 25-35 (1989).
Williams et al., *Abstract of Paper*, Microbiology of Poultry Waste Digestion and Discovery of a Feather Degrading Microorganism, Dept. of Poul. Sci., N. C. State University, Raleigh, NC 27695.
Vallalat, *Chemical Abstracts*, 108, 516 (1988).
Daniels, *J. Gen. Microbiol.*, 8, 289-294 (1953).
Williams et al., *J. Appl. Bacteriol.*, 67, 25-35 (1989).
"Maxacal ™ L, High Alkaline Protease Liquid," Gist-Brocades USA, Inc.
"Alcalase 2.4L." Proteolytic Enzyme Prepared by Submerged Fermentation of a Selected Strain of *Bacillus Licheniformis*. Novo Laboratories, Inc.

Primary Examiner—Robert A. Wax
Assistant Examiner—Keith D. Hendricks
Attorney, Agent, or Firm—Bell, Seltzer, Park & Gibson

[57] ABSTRACT

A substantially pure keratinaceous material-degrading *B. licheniformis* PWD-1 enzyme is disclosed. The substantially pure enzyme is characterized by a molecular weight of 33 kiloDaltons, an isoelectric point of 7.25, an optimum pH of 7.5, an optimum temperature of 45°–50° C., and thermal stability at low temperatures.

1 Claim, 11 Drawing Sheets

1: pH STANDARDS
2: KERATINASE

MARKER   −20°C   4°C   25°C

FIG. 11.

PURIFIED *BACILLUS LICHENIFORMIS* PWD-1 KERATINASE

RELATED APPLICATIONS

This application is a continuation-in-part of the application of Jason C. H. Shih and C. Michael Williams, filed Sep. 13, 1990, Ser. No. 07/581,681 now U.S. Pat. No. 5,163,161 entitled "Method of Degrading Keratinaceous Material and Bacteria Useful Therefor," which is a continuation of Jason C. H. Shih and C. Michael Williams, "Method of Degrading Keratinaceous Material and Bacteria Useful Therefor," Ser. No. 175,476, filed Mar. 31, 1988, now U.S. Pat. No. 4,959,311, issued Sep. 25, 1990.

FIELD OF THE INVENTION

The present invention relates to a substantially pure keratinaceous material-degrading enzyme obtained from *Bacillus licheniformis* PWD-1.

BACKGROUND OF THE INVENTION

Feathers are produced in large quantities by the poultry industry. These feathers provide an inexpensive source of raw material for a variety of potential uses. Among other things, there has been considerable interest in developing methods of degrading feathers so they can be used as an inexpensive source of amino acids and digestible protein in animal feed.

Processes for converting feather into animal feed which have been developed to date include both steam hydrolysis processes and combined steam hydrolysis and enzymatic processes. See, e.g., Papadopoulos, M.C., Animal Feed Science and Technology 16, 151 (1986); Papadopoulos, M. C. et al., Poultry Science 64, 1729 (1985); Alderibigde, A. O. and D. Church, J. Anim. Sci., 1198 (1983); Thomas and Beeson, J. Anim. Sci. 45, 819 (1977); Morris and Balloun, Poultry Sci. 52, 858 (1973); Moran et al., Poultry Sci. 46, 456 (1967); Davis et al., Processing of poultry by-products and their utilization in feeds. Part I. USDA Util. Res. Rep. no. 3, Washington, D.C. (1961). Disadvantages of these procedures, such as the degradation of heat sensitive amino acids by steam processes and the relatively low digestibility of the resulting products, have lead to continued interest in economical new feather degradation procedures which do not require a harsh steam treatment.

Accordingly, an object of the present invention is to provide a process for hydrolyzing keratinaceous material which does not depend upon steam hydrolysis.

An additional object is to provide a process for converting keratinaceous material into amino acids at high yields of the amino acids.

A further object of this invention is to provide a hydrolyzed feather product useful as a feed ingredient which is highly digestible and provides a good quality source of dietary protein and amino acids.

A still further object of the present invention is to provide an economical animal feed which employs a hydrolyzed feather product as a dietary amino acid source.

The foregoing and other objects and aspects of the present invention are explained in detail in the Summary, Detailed Description, and Examples sections below.

SUMMARY OF THE INVENTION

A first aspect of the present invention is a method of degrading keratinaceous material. The method comprises the steps of combining keratinaceous material with *B. licheniformis* to form a fermentation media, and then fermenting the media for a time sufficient to degrade the material. In addition to degrading keratinaceous material, the method of the present invention can be used to produce amino acids. In this case, a fermentation media produced as described above is fermented for a time sufficient to produce free amino acids therefrom, and the free amino acids are recovered from the media.

The method of the present invention can also be used to produce a hydrolyzed feather product. In this latter case, a fermentation media produced as described above, with feather as the keratinaceous material, is fermented for a time sufficient to increase the digestibility of the media (e.g., by enriching the concentration of digestible proteins and peptides therein). Preferably, the bacteria in the media are then killed to form a hydrolyzed feather product useful as a feed ingredient (i.e., the media with the bacteria are treated to kill the bacteria).

When the method of the present invention is used to produce free amino acids or a hydrolyzed feather product, the fermentation step is preferably an anaerobic fermentation step. Under anaerobic conditions, *B. licheniformis* does not actively grow. Hence, the utilization of amino acids by *B. licheniformis* is decreased and free amino acid production, or enrichment, is increased. In addition, prior to the step of combining the feathers with *B. licheniformis*, *B. licheniformis* is preferably first grown under aerobic conditions (preferably in a liquid culture) to obtain enriched quantities of active bacteria. These procedures, as explained in detail below, provide an efficient and cost-effective way to degrade keratinaceous material and to utilize feather.

A second aspect of the present invention is a pure culture of the keratinaceous material-degrading microorganism having the identifying characteristics of *B. licheniformis* PWD-1, ATCC No. 53757. *B. licheniformis* PWD-1 is the preferred microorganism for carrying out the methods described above.

A third aspect of the present invention is a hydrolyzed feather product, which may be produced by the method described above. This product comprises partially hydrolyzed feather, proteins cleaved from the partially hydrolyzed feather, peptides cleaved from the partially hydrolyzed feather, and *B. licheniformis* cells (preferably killed *B. licheniformis* cells). This hydrolyzed feather product may be combined with a carbohydrate source and, preferably, minerals and vitamins, to form an animal feed. A second, supplementary protein source may optionally be included in the feed.

Additional aspects of the present invention are discussed below.

DETAILED DESCRIPTION OF THE INVENTION

The present invention can be carried out with all types of keratinaceous material, including hair, hooves, and feather. Feather is preferred. Any type of feather may be employed, including chicken, turkey, and duck feather. Chicken feather is preferred, and is the material recited in the text which follows. However, the teaching of this text is applicable to the degradation and utilization of all keratinaceous materials.

Prior to combining feather with *B. licheniformis* to form a fermentation medium, the feather should be sterilized to kill bacteria naturally present on the feather which might otherwise disrupt the fermentation process. This sterilization step may be carried out by any means, including fumigation by contacting feather to formalin or ethylene oxide gas, by contacting feather to steam under pressure, or by combinations of the same. We have found that, by contacting feather to steam under pressure, even for a time insufficient to sterilize the feather, subsequent bacterial degradation of the feather is substantially improved. Accordingly, sterilization steps in the present invention preferably include a step of contacting the feather to steam for a time and at a temperature sufficient to facilitate the subsequent bacterial hydrolysis thereof, even if this steam treatment step does not accomplish a complete sterilization of the feather. We have found that contacting feather to steam under pressure, in an enclosed chamber, at 125 degrees Centigrade for a time as brief as 2 minutes is sufficient to substantially enhance the subsequent fermentation hydrolysis thereof. If sterilization of feather should be carried out solely by steam, the feather should be contacted to steam under pressure at 125 degrees Centigrade for at least 15 minutes (a 15–20 minute treatment at this temperature being, by definition, an autoclaving step). The time and temperature of steam treatment should be less than those employed in commercial steam hydrolysis processes, which employ treatment times of 35 minutes or more at steam pressures of about 35 p.s.i. or more.

Prior to fermentation, *B. licheniformis* can be grown aerobically in any suitable liquid growth medium (preferably a feather-based liquid growth medium). The bacteria is preferably grown at a temperature of from about 45 to about 55 degrees centigrade. After a sufficient quantity of the bacteria is grown (preferably about $10^8$ colony forming units per milliliter), the liquid growth medium is combined with feather in any suitable fermentation vessel. Preferably, the liquid growth medium and feather are combined at a high proportion of feather, so that the fermentation is a semi-solid fermentation. A preferred fermentation media comprises, by weight, at least about 1 part of dry feather per 4 parts of liquid growth medium, or more preferably about 1 part of dry feather per 2 parts of liquid growth medium.

Carbohydrate sources used to produce an animal feed according to the present invention include, for example, corn, oats, barley, sorghum, or combinations of the same. These grains are preferably ground into a meal for use in the animal feed. Supplementary protein sources include, for example, soy meal, fish meal, blood meal, poultry by-product (ground poultry offal), meat meal, and combinations of the same. An animal feed is comprised of from about 13% to about 25% by weight of protein from all protein sources (both hydrolyzed feather and supplemental). The hydrolyzed feather product may be the sole protein source, but is preferably from about 2% to about 15% by weight of the feed. Other nutrients in small amounts, such as vitamins, minerals, antibiotics, and other substances or compounds may be included in the feed as required.

*B. licheniformis* strain PWD-1 was deposited with the American Type Culture Collection in accordance with the Budapest Treaty on March 23, 1988, and has been assigned ATCC Accession No. 53757.

PWD-1 has been found to be a gram positive (but gram variable) bacteria. It is a straight rod-shaped bacteria, the rods being from about 2.1 to about 3.0 microns long and from about .5 to about 1.0 microns wide, with the ends of the rods being rounded. Bacterial cells are found both singly and in chains. One subterminal endospore is formed per cell, the endospore being centrally located and round or oval in shape.

PWD-1 forms opaque, entire (mucoid) colonies which are erose and irregular in shape. Low convex, high convex (mucoid) and flat colonies are seen. Colonies are seen to disassociate. The colonies are observed as glistening (mucoid) dull, dry, smooth (mucoid) and rough, with an insoluble brown pigment present. Cells are motile (flagella being present) and peritrichous.

PWD-1 grows at temperatures of from about 20° C. to about 55° C., with trace growth being present at 60° C. In our hands, the bacteria is thermophilic, growing best at temperatures of from 45° C. to 50° C. Others have reported an optimum growth range of between 21° C. and 30° C. for other strains of *B. licheniformis*.

PWD-1 produces acid, but not gas, from L-arabinose, D-xylose (weakly), D-glucose, lactose (weakly), sucrose, and D-mannitol. It can utilize both citrate and propionate as a carbon source. PWD-1 hydrolyzes polysaccharide, starch and casein, but not hippurate. PWD-1 liquifies gelatin. It reduces, but does not reoxidize, methylene blue. It reduces nitrate to nitrite, but it does not reduce nitrite.

PWD-1 is Voges Proskauer (5198) positive, Voges Proskauer (5198 fil) positive, and Voges Proskauer (5331) positive. It decomposes hydrogen peroxide but not tyrosine, is negative for indole, and is positive for dihydroxyacetone. PWD-1 is negative in the Litmus milk acid test, negative in the Litmus milk coagulation test, and negative in the Litmus milk alkaline test, but is positive in both the litmus milk peptonization and litmus milk reduction tests.

PWD-1 grows at a pH of 5.7 and at a pH of 6.0. It shows a pH VP5198 of 8.0 or more. The optimum pH in nutrient broth is 7.0 to 7.5. It is aerobic and facultative. It does not grow in 0.02% azide. It generates gas from sealed nitrate and grows in sealed glucose. It is negative for lecithinase.

A crude, cell-free extract comprised of a mixture of *B. licheniformis* PWD-1 proteins capable of degrading keratinaceous material is also an aspect of the present invention. This crude extract is prepared, for example, by separating *B. licheniformis* PWD-1 cells from their liquid growth media, the liquid growth media so becoming the crude cell-free extract. Alternatively, *B. Licheniformis* PWD-1 cells may be lysed (chemically or physically) in a liquid growth media to produce a crude, cell-free extract. Other means of preparing such an extract will be apparent to persons skilled in the art. The crude, cell-free extract may be provided in aqueous form. Alternatively, it may be provided in lyophilized form to increase the shelf life thereof.

A substantially pure, keratinaceous material-degrading, *B. licheniformis* PWD-1 enzyme is a further aspect of the present invention. This substantially pure enzyme is produced by separating the proteins which comprise the crude, cell-free extract described above into its individual, constituent proteins. Any suitable separation procedure may be employed. Numerous such separation procedures, such as column chromatography, are known to and routinely employed by persons skilled in the art for this purpose. The individual constituent proteins are then screened for their ability to degrade keratinaceous material. That constituent protein which best degrade keratinaceous material comprises the substantially pure enzyme. Like the crude cell-free extract, the substantially pure enzyme may be provided in either aqueous or lyophilized form.

Both the crude cell-free extract and the substantially pure enzyme, when provided in aqueous form, may be used to degrade keratinaceous material (preferably feather) by combining the same with the keratinaceous material to form a fermentation media, and then fermenting the fermentation media for a time sufficient to degrade the feathers.

A still further aspect of the present invention is a DNA sequence comprising a cloned gene or fragment thereof which codes for the production of a keratinaceous material-degrading *B. licheniformis* PWD-1 enzyme or active fragment thereof. This cloned gene is produced as follows. First, a multiplicity of *B. licheniformis* PWD-1 DNA sequences are generated (as either a genomic DNA or complementary DNA library). These sequences are then inserted into DNA expression vectors to form recombinant expression vectors. Next, the recombinant expression vectors are inserted into suitable hosts to form transformants which express the DNA sequences. Finally, these transformants are screened for the production of a keratinaceous material-degrading enzyme. Transformants which express such an enzyme carry, as an insertion in the vector contained therein, the desired DNA sequence.

A multiplicity of *B. licheniformis* PWD-1 DNA sequences may be generated by conventional techniques. One approach is to digest the genomic DNA of an *B. licheniformis* PWD-1, with the ultimate goal being the preparation of a genomic DNA library. See generally R. Old and S. Primrose, Principles of Gene Manipulation, 102-109 (3d ed. 1985). Another approach is to isolate mRNA from *B. licheniformis* PWD-1 and generate cDNA sequences therefrom, with the ultimate goal being the preparation of a cDNA library. See generally R. Old and S. Primrose, supra at 109-111; T. Maniatis, E. Fritsch and J. Sambrook, Molecular Cloning: A Laboratory Manual, 187-246 (1982).

A variety of vector-host combinations may be employed to produce the cloned gene. Host cells may be either prokaryotic or eukaryotic cells, and, when the host cells are bacterial cells, they may be either gram negative or gram positive bacteria. Useful hosts include, for example, *Escherichia coli* (including, for example, *E. coli*, X1776, *E. coli* X2282, *E. coli* HB101 and *E. coli* MRC1), species of Salmonella (including, for example, *S. typhimurium*, *S. enteriditis*, and *S. dublin*) species of Pseudomonas (including, for example, *P. aeruginosa* and *P. putida*), and *Bacillus subtilis.*

Vectors used in practicing the present invention are selected to be operable as cloning vectors or expression vectors in the selected host cell. The vectors may, for example, be bacteriophage, plasmids, viruses, or hybrids thereof. Vectors useful in *E. coli* include plasmids (for example, pSC101, ColEI, RSF2124, pBR322, pBR324, pBR325, pAT153, pUC-6 and pUC-8), bacteriophage lambda, cosmids, phasmids, and filamentous coliphages. Salmonella species may be transformed, for example, with plasmids such as pJC217, pBRD001, and pBRD026. Vectors useful in gram negative bacteria generally include plasmids of incompatibility groups P, Q or W, which have broad host ranges (for example, Sa, RP4, and RSF1010), and Transposons such as TnT. *Bacillus subtilis*, a gram positive bacteria, can be transformed with *S. aureus* plasmids (for example, pC194, pE194, pSA0501, pUBI10, and pT127).

Within each specific vector various sites may be selected for insertion of the isolated DNA sequence. These sites are usually designated by the restriction enzyme or endonuclease that cuts them. For example, in pBR322 the Pst I site is located in the gene for penicillinase between the nucleotide triplets that code for amino acids 181 and 182 of the penicillinase protein.

*B. licheniformis* PWD-1 DNA sequences may be inserted into the desired vector by known techniques. If, however, the vector is to serve as an expression vector, the vector should have a promoter, and the DNA sequence should be inserted in the vector downstream of the promoter and operationally associated therewith. The vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the *B. licheniformis* PWD-1 DNA sequence once inserted (preferably, in correct translational reading frame therewith). The vector should be selected to provide a region which codes for a ribosomal binding site recognized by the ribosomes of the host cell into which the vector is to be inserted. For example, if the host cell is to be a prokaryotic cell such as *E. coli*, then the region which codes for a ribosomal binding site may code for a Shine-Dalgarno sequence.

Transformants may be screened for the production of keratinaceous material-degrading enzyme, or active fragment thereof, by any convenient procedure. Preferably, the transformants are grown on an agar medium containing powdered keratin substrate. Any powdered keratin may be used, but powdered feather is preferred, particularly powdered white feather, on which a clearing zone is easiest to observe. Colonies showing a clearing zone on the medium are producing the desired enzyme or enzyme fragment.

The present invention is explained further in the following examples. These examples are provided for illustrative purposes only, and are not to be taken as limiting.

EXAMPLE 1

Comparison of Amino Acid Production By Aerobic and Anaerobic Fermentations

*B. licheniformis* PWD-1 was grown in two batches of a sterile aqueous medium containing feather as the sole source of carbon and energy. Each liter of medium contained 0.5 grams of $NH_4Cl$, 0.5 grams of NaCl, 0.3 grams of $K_2HPO_4$, 0.4 grams of $KH_2PO_4$, 0.24 grams of $MgCl_2 5.46H_2O$, 1.0 grams of hammer-milled feather (a coarsely chopped feather) and 0.1 grams of yeast extract. The media were adjusted to a pH of 7.5. Each culture was incubated at 50 degrees Centigrade, one being grown under aerobic conditions and the other being grown under anaerobic conditions. The quantity of amino acids found in the media at day zero (prior to inoculation) and after five days of incubation both aerobic and anaerobic conditions, is shown in Table 1 below.

TABLE 1

Free amino acid concentrations in the growth medium of feather degrading microorganisms under aerobic and anaerobic conditions.

| Amino Acid (mg/l) | Day 0 | Day 5 Aerobic | Anaerobic |
| --- | --- | --- | --- |
| ASP (N) | 0.00 | 0.00 | 3.40 |
| THR | 0.78 | 0.90 | 9.00 |
| SER | 0.83 | 1.10 | 7.60 |
| GLU (N) | 0.00 | 1.70 | 11.80 |
| GLY | 1.61 | 0.50 | 6.60 |
| ALA | 1.35 | 1.10 | 14.50 |
| CYS | 0.11 | 3.00 | 10.20 |
| VAL | 0.36 | 2.10 | 17.10 |
| MET | 0.00 | 1.90 | 4.60 |
| ILE | 0.19 | 1.70 | 20.70 |
| LEU | 0.91 | 2.10 | 32.60 |
| TYR | 0.00 | 0.00 | 6.30 |
| PHE | 0.00 | 3.30 | 22.40 |
| ORN | 0.00 | 0.70 | 7.50 |
| LYS | 0.99 | 3.10 | 6.80 |
| HIS | 0.22 | 0.00 | 2.70 |
| ARG | 1.05 | 1.00 | 11.20 |
| TOTAL | 8.40 | 24.20 | 195.00 |

These data show that the total production of amino acids was approximately 800% greater under anaerobic conditions than under aerobic conditions.

EXAMPLE 2

Amino Acid Yields in Semi-Solid Fermentations

PWD-1 was grown in a liquid media like that described in Example 1 (except that 10.0 grams of hammer milled feather per liter was used instead of 1.0 gram/liter) for 5 days at 50 degrees Centigrade under aerobic conditions to reach 10a CFU per milliliter. An additional quantity of hammer milled feathers was autoclaved with steam at 125 degrees Centigrade (16 p.s.i.) for 15 minutes. The feathers were mixed with the growth medium at a proportion of 250 grams feather per liter of growth medium in a fermentation vessel to form a fermentation medium, and the fermentation medium was flushed with nitrogen. The fermentation medium was then incubated anaerobically for five days at 50 degrees Centigrade with periodic agitation. The same procedure was carried out on a separate occasion, except that the fermentation step was carried out aerobically. These procedures were duplicated for both conditions. The amino acid concentrations in the liquid phase of all the fermentation media were measured on day five of fermentation, these data being given in Table 2 below.

TABLE 2

Total free amino acid concentrations (g/l) in the liquid phase of the semi-solid phase fermentations

| Fermentation | Anaerobic | Aerobic |
| --- | --- | --- |
| 1 | 14.7 | 1.7 |
| 2 | 12.4 | 1.9 |

Note that, under anaerobic conditions, free amino acids are produced in quantities in excess of 10 grams/liter by semi-solid phase fermentations.

EXAMPLE 3

Production of a Hydrolyzed Feather Meal Feed Product

After five days of anaerobic fermentation, a semi-solid fermentation medium like that described in Example 2 above was autoclaved with steam at 125 degrees Centigrade for 15 minutes, then dried at 60 degrees Centigrade for 48 hours, and then milled through a one millimeter mesh. The resulting product was a brown powder comprised of partially hydrolyzed feather, short peptides, amino acids, and killed *B. licheniformis* bacterial cells. This product is useful, among other things, as a dietary source of protein for growing chickens, as shown in Example 4 below.

EXAMPLE 4

Animal Feeds Incorporating *B. Licheniformis* Hydrolyzed Feather

One hundred and twenty-eight chicks were divided into four equal groups, 4×8 in each group. Each group was raised on a different diet: group (a) was raised on corn-soy feed/20% protein; group (b) was raised on corn-soy feed/15% protein; group (c) was raised on corn-soy feed/15% protein plus 5% unhydrolyzed hammer-milled feather; group (d) was raised on corn-soy feed/15% protein plus 5% protein from *B. licheniformis* hydrolyzed feather produced in accordance with the procedure described in Example 3 above. All birds were weighed at three weeks of age and the weights for each group averaged. These averages are shown in Table 3 below.

TABLE 3

Ability of Growing Chickens to Utilize Feather-lysate as a Dietary Protein Source.

| Diet | Mean Body Weight (grams) M + SEM |
|---|---|
| Standard corn-soy, 20% protein | 554.7 ± 8.5 |
| Standard corn-soy, 15% protein | 503.9 ± 8.3 |
| Corn-soy, 15% protein + 5% protein from untreated feathers | 458.8 ± 7.1 |
| Corn-soy, 15% protein + 5% protein from feather-lysate | 525.6 ± 8.9 |

These data show that *B. licheniformis* hydrolyzed feather can be used as an inexpensive source of dietary protein in animal feed.

EXAMPLE 5

Development of Assay for Keratinase Activity

The test described below was developed in order to simplify analytical work on keratinase. Azo-keratin hydrolysis provides a colorimetric assay for enzymatic activity on keratin.

Synthesis and Enymatic Hydrolysis of Azo-keratin (i) Synthesis. Azo-keratin was prepared by a similar method similar to a known procedure for azoalbumin. See, e.g. Tomarelli, Charney & Harding, The use of azoalbumin as a substrate in the colorimetric determination of peptic and tryptic activity 434 J. Lab. Clin. Med. 428 (1949). Ball-milled feather powder was prepared as described in Williams & Shih, Enumeration of some microbial groups in thermophilic poultry waste digesters and enrichment of a feather-degrading culture, 67 J. Appl. Bacteriol. (1989). A 1 g portion of the feather powder (the keratin source) was placed in a 100-ml round-bottomed reaction flask with 20 ml of deionized water. The suspension was mixed with a magnetic stirrer. Two ml of 10% $NaHCO_3$ (weight per volume) were mixed into the feather suspension. In a separate 10-ml tube, 174 mg of sulfanilic acid (Chemical Dynamics Corp., South Plainfield, N.J. 07080, U.S.A.) were dissolved in 5 ml of 0.2 N NaOH. Sixty-nine mg of $NaNO_2$ were then added to the tube and dissolved. The solution was acidified with 0.4 ml of 5 N HCl, mixed for 2 min and neutralized by adding in 0.4 ml of 5 N NaOH. This solution was added to the feather keratin suspension and mixed for 10 min. The reaction mixture was filtered and the insoluble azo-keratin was rinsed thoroughly with deionized water. The azo-keratin was suspended in water and shaken at 50° C. for 2 hr and filtered again. This wash cycle was repeated until the pH of the filtrate reached 6.0-7.0 and the spectrophotometric absorbance of the washing at 450 nm was less than 0.01. Finally, the wash cycles were repeated at least twice using 50 mM potassium phosphate buffer, pH 7.5. The azo-keratin was washed once again with water and dried in vacuo overnight at 50° C. The resulting product is a chromogenic substrate that can be incubated with enzyme solution to produce and release soluble peptide derivatives that cause an increase in light absorbance of the solution.

(ii) Enzymatic hydrolysis of azo-keratin. This procedure tested the keratinolytic activity of keratinase, collagenase, elastinase, proteinase K, and papain on azo-keratin. To begin the process, 5 mg of azo-keratin was added to a 1.5-ml centrifuge tube along with 0.8 ml of 50 mM potassium phosphate buffer, pH 7.5. This mixture was agitated until the azo-keratin was completely suspended. A 0.2-ml aliquot of an appropriately diluted enzyme sample was added to the azo-keratin, mixed and incubated for 15 min at 50° C. with shaking. Assay conditions were the same for each enzyme sample except that pH and temperature were adjusted to their optima for the specific enzyme. The reaction was terminated by adding 0.2 ml of 10% trichloroacetic acid (TCA). The reaction mixture was filtered and analyzed for activity.

The absorbance of the filtrate was measured at 450 nm with a UV-160 spectrophotometer (Shimadzu, Columbia, Md., 21046, U.S.A.). A control sample was prepared by adding the TCA to a reaction mixture before the addition of enzyme solution. A unit of keratinase activity was defined as a 0.01 unit increase in the absorbance at 450 nm as compared to the control after 15 min of reaction.

Table 4 presents the results of hydrolysis of azo-keratin by the different enzymes. Hydrolytic activity is presented in both absolute terms (specific activity), measured by light absorption at 450 nm after 15 minutes of reaction, and in relation to the other enzymes (relative activity), in which the activity of the most active protease is assigned a value of 100 and the activity of the others is scaled down proportionately. Keratinase demonstrated the greatest activity toward azo-keratin, showing a specific activity of 4465 units/mg. The other proteases showed no more than 26% (proteinase K) of the specific activity of keratinase. Collagenase and papain were not active with the azo-keratin substrate. The results indicate an exceptional specificity between keratinase and azo-keratin, thus validating the use of this test an assay for keratinase activity.

TABLE 4

| | Hydrolysis of azo-keratin by different proteolytic enzymes | | | | | |
|---|---|---|---|---|---|---|
| | Papain | Trypsin | Collagenase | Elastase | Proteinase K | Keratinase |
| pH | 6.2 | 7.6 | 7.5 | 8.8 | 7.5 | 7.5 |
| Temp. (C.°) | 25 | 25 | 37 | 37 | 37 | 50 |
| Specific Activity (U*/mg protein) | 0.0 | 688 | 0.0 | 788 | 1163 | 4465 |
| Relative Activity | 0 | 15 | 0 | 18 | 26 | 100 |

*An enzyme unit (U) is an increase of 0.01 in absorbance at 450 nm after reaction with azo-keratin for 15 min.

EXAMPLE 6

Purification of Keratinase

This example describes the purification of the keratinase that is secreted by the feather-degrading *B. licheniformis* PWD-1.

Organism and Growth Conditions

All culture conditions and feather are described above. The culture medium contained the following ingredients: 0.5 g/l $NH_4Cl$; 0.5 g/l NaCl; 0.3 g/l $K_2HPO_4$; 0.4 g/l $KH_2PO_4$; 0.1 g/l $MgCl_2.6H_2O$; 0.1 g/l yeast extract and 10 g/l hammer-milled feathers. The pH was adjusted to 7.5. Feathers were washed, dried, and hammer-milled prior to being added to the medium. The medium was sterilized by autoclaving.

The bacterium was cultured in test tubes (20 cm ×1.5 cm) containing 10 ml of culture medium each. After a 4-day incubation, the 10-ml culture medium was transferred to a 3-liter Fermbach flask containing 1.0 liter culture of medium. After a second 4-day incubation, the medium was collected for keratinase purification. Both incubations were conducted at 50° C. with shaking at 120 rpm in a Controlled Environment shaker (New Brunswick Scientific Co., New Brunswick, N.J., U.S.A.).

Enzyme Purification (i) Filtration and concentration. The culture medium was prefiltered with glass wool to remove residual undegraded feathers. The medium was then filtered through a 0.45 μm membrane using the Millipore Pellicon Cassette System (Millipore Corporation, Bedford Mass. 01730, U.S.A.) to remove bacterial cells and other particles. The filtrate was concentrated by membrane ultrafiltration (MW >10,000 dalton) using the same cassette system.

(ii) Ion exchange chromatography. The crude concentrated keratinase solution was introduced into a CM-cellulose column (2.5 cm×60 cm). The column was equilibrated first with buffer A (25 mM potassium phosphate buffer, pH 5.8). Approximately 50 mg of filtrate was loaded on the column. Elution at a rate of 0.4 ml/min began with 500 ml of buffer A. The eluted proteins were monitored by measuring the absorbance of the fractions at 280 nm. When the spectrophotometric reading of 280 nm was a continuous baseline, thus indicating a complete absence of protein in elution, a second elution began at the same flow rate with approximately 300 ml of buffer B (25 mM potassium phosphate buffer, pH 6.2; 20 mM NaCl). Finally, buffer C (25 mM potassium phosphate buffer, pH 6.8; 20 mM NaCl) was used to elute the enzyme at this same flow rate. Five-ml fractions were collected and screened using the azo-keratin hydrolysis test. Keratinase active fractions were pooled and concentrated with an Amicon stirred cell filtration system using Diaflo ultrafilters (MW >10,000 Da) (Amicon Division, W. R. Grace and Co., Beverly, Mass. 01915, U.S.A.) at 4° C.

(iii) Gel filtration chromatography. Purification of keratinase active fractions was continued with a Sephadex G-75 gel filtration column (1.5 cm×90 cm). Equilibration and elution were carried out at 4° C. with 50 mM potassium phosphate buffer, pH 7.0 at a flow rate of 0.3 ml/min. Fraction volumes of 3 ml were collected. Protein elution was followed by measuring the spectrophotometric absorbance of each fraction at 280 nm. As described above, fractions were assayed for keratinase activity with the azo-keratin hydrolysis test. The keratinase active fractions were pooled and concentrated with the Amicon stirred cell unit.

After each step the protein concentration in aqueous solution was measured. Measurements were taken by the Bio-rad Protein Assay method as described by Bradford, A rapid and sensitive method for the quantitation of microgram quantities of protein utilizing the principle of protein-dye binding. 72 Anal. Biochem. 248 (1976).

Results of Keratinase Purification

Results shown in Table 5 confirm the purification of keratinase from the medium of *B. licheniformis* PWD-1. Purification was calculated by dividing the specific activity of the enzyme after purification by the specific activity of the original bacterial medium. The invention thus provides a substantially pure, keratinaceous material-degrading, *B. lichenformis* PWD-1 enzyme having an overall purification factor from 1.5 to 90 fold, more particularly having a purification factor from 10 to 80 fold and most particularly having a purification factor of 55 to 75 fold. The enzyme has a specific activity from about 100 to 10,000, more particularly has a specific activity from 1000 to 8000, and most particularly has a specific activity from about 5,000 to 6,500. The purified enzyme can be provided in aqueous solutions having concentrations ranging from 0.05 to 5 mg/ml, and more particularly having concentrations from 0.1 to 1 mg/ml, but various concentrations can be prepared by concentration and dilution procedures known to those skilled in the art of protein purification.

Figure 1:
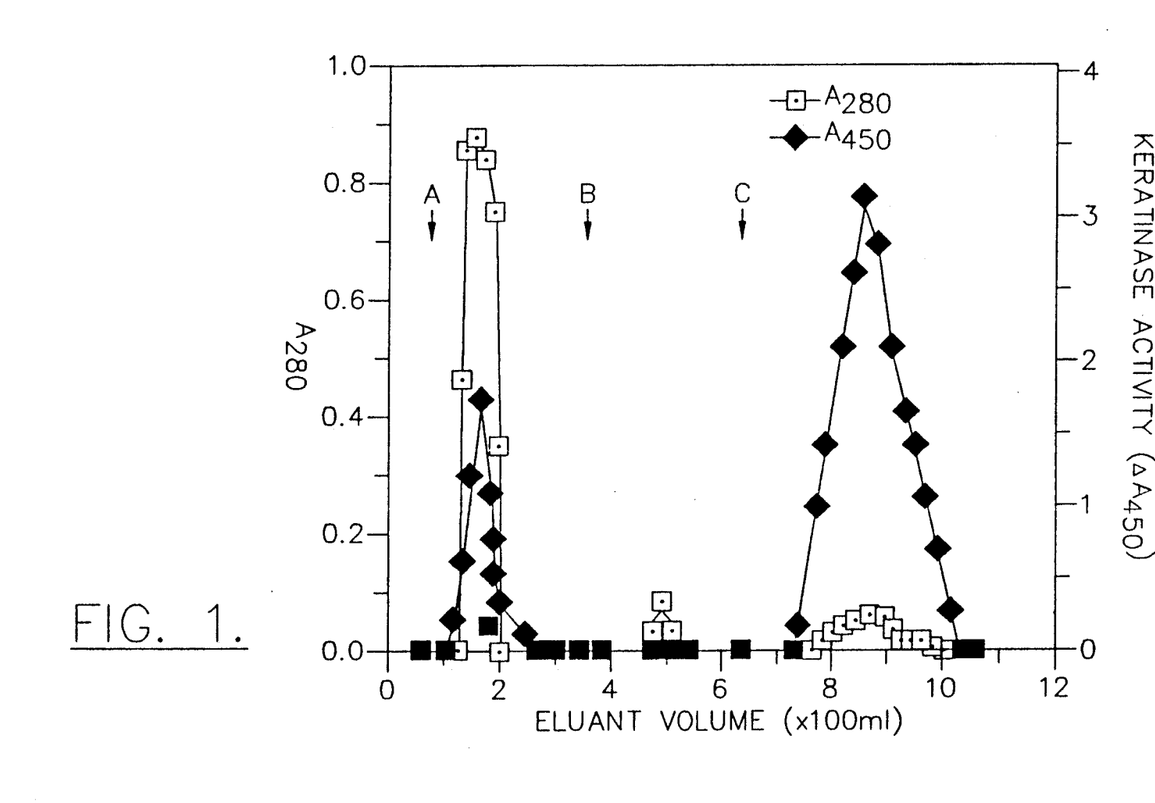
FIG. 1 shows the results of CM-cellulose chromatography of keratinase purified from bacterial medium.

It is useful to examine the effect of the individual steps of the purification process. The concentrated fraction produced by ultrafiltration removed approximately 60% of the total protein present in the medium while maintaining 70% of the enzymatic activity. FIG. 1 shows the elution profile for keratinase from ion exchange chromatography. Although keratinase activity was detected in two peaks, the second peak, eluted in buffer C with 20 mM NaCl, pH 6.8, showed most of the total activity and a greater specific activity.

TABLE 5

| Purification of keratinase from the medium of *B. licheniformis* PWD-1 | | | | |
|---|---|---|---|---|
| | Medium | Concentrated Medium | CM-Cellulose | Sephadex G-75 |
| Volume (ml) | 400 | 85 | 32 | 4.6 |
| Protein Conc. (mg/ml) | 0.36 | 0.64 | 0.11 | 0.33 |
| Total Protein (mg) | 142 | 54.5 | 3.3 | 1.5 |
| Total Activity (U) | 12,200 | 8,450 | 12,080 | 8,910 |
| Specific Activity (U/mg. protein) | 86 | 150 | 3,720 | 5,990 |
| Yield of Protein (%) | 100 | 38.4 | 2.30 | 1.05 |
| Yield of Enzyme (%) | 100 | 69.3 | 99.0 | 73.1 |
| Fold of Purification | 1.0 | 1.8 | 43.3 | 69.6 |

*An enzyme unit (U) is an increase of 0.01 in absorbance at 450 nm after reaction with azo-keratin for 15 min.

Figure 2:
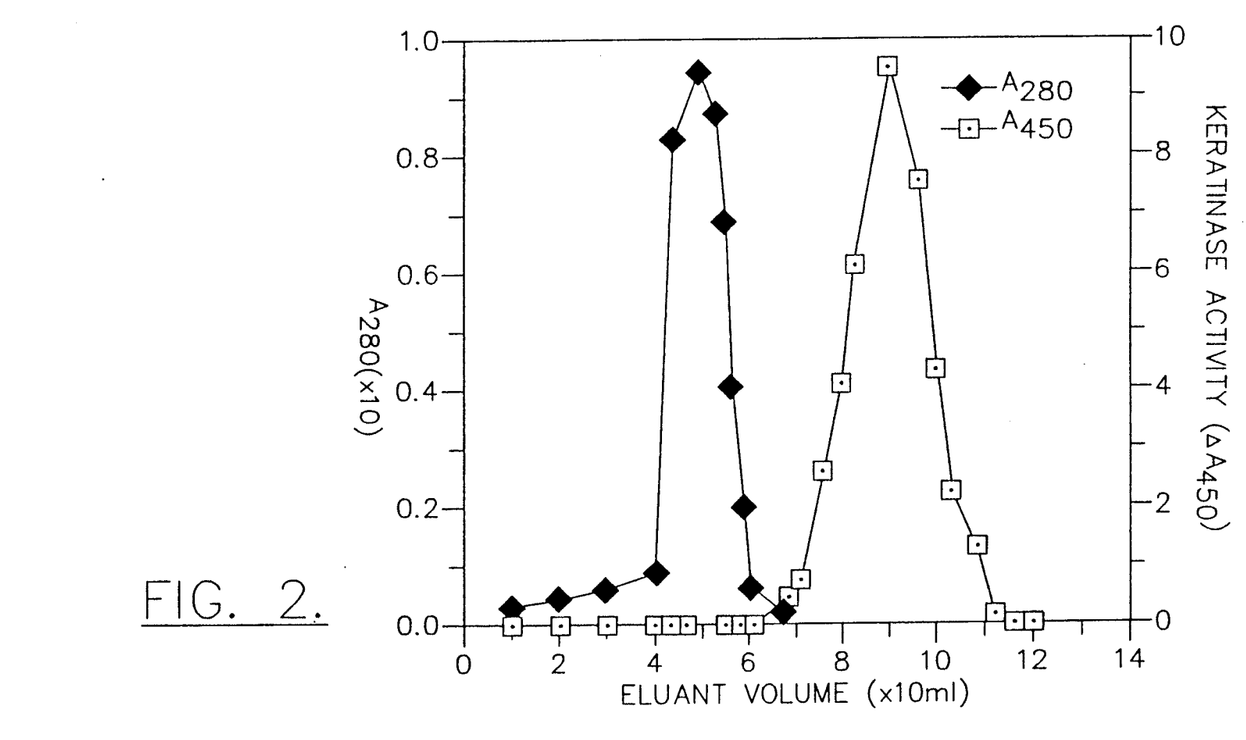
FIG. 2 shows the results of Sephadex G-75 column chromatography of keratinase purified from bacterial medium.

The active fractions of the second peak were pooled and concentrated. Assay results show a 43-fold purification increase and a 98% decrease in total protein due to this step, suggesting that it was the most efficient purification step. The elution profile of keratinase under gel filtration chromatography is shown in FIG. 2. After pooling and concentrating these keratinase active fractions, the final product yielded a homogeneous protein as shown by the single band on the SDS-polyacrylamide gel (Lanes 1 and 3 of FIG. 5).

EXAMPLE 7

Characterization of Keratinase

This example reports physical and biochemical properties of purified keratinase.

Molecular Weight Determination (i) Estimation of the molecular weight by gel filtration. To estimate the native molecular weight (MW) of keratinase, a Sephadex G-75 column was calibrated with standard proteins from a kit obtained from Pharmacia Fine Chemicals (Piscataway, N.J., U.S.A.). The molecular weight standards were: BSA, 67 kDa; ovalbumin, 43 kDa; chymotrypsinogen A, 25 kDa, and ribonuclease A, 13.7 kDa. Blue dextran was used for estimating the void volume of the column.

Figure 3:
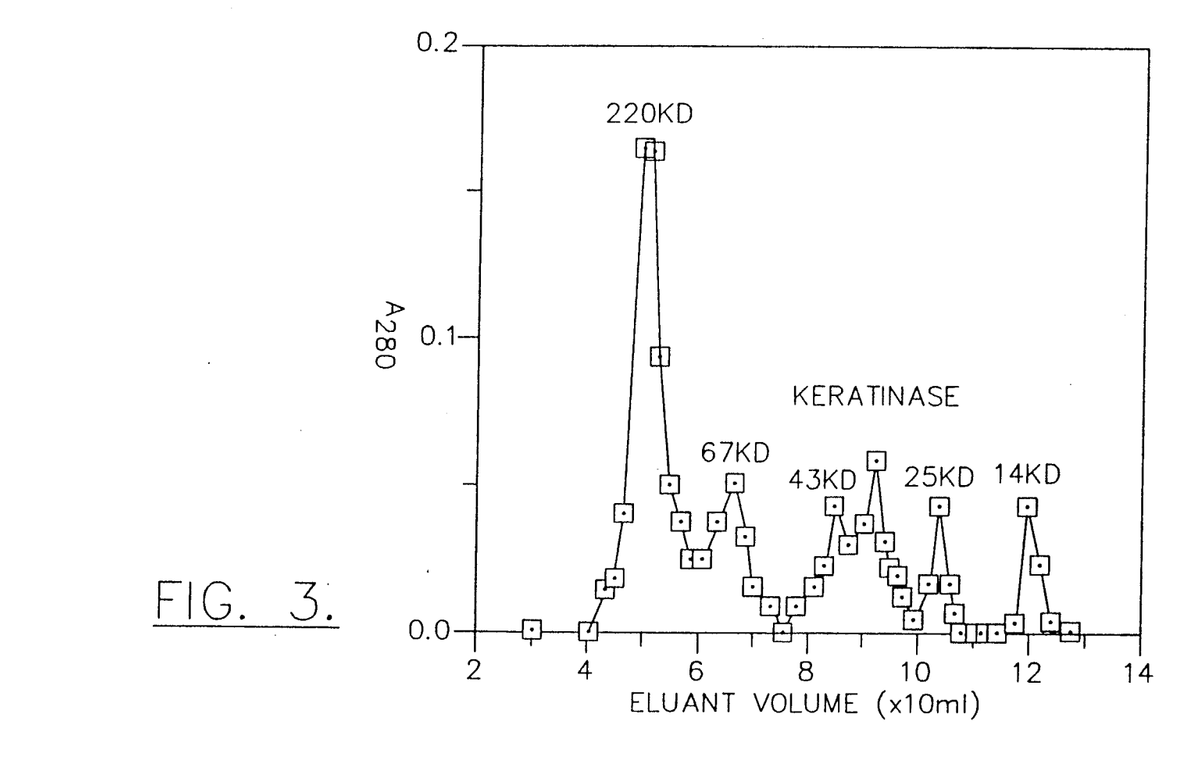
FIG. 3 shows the elution profile of keratinase mixture and molecular weight standards using Sephadex G-75 column gel filtration chromatography.
Figure 4:
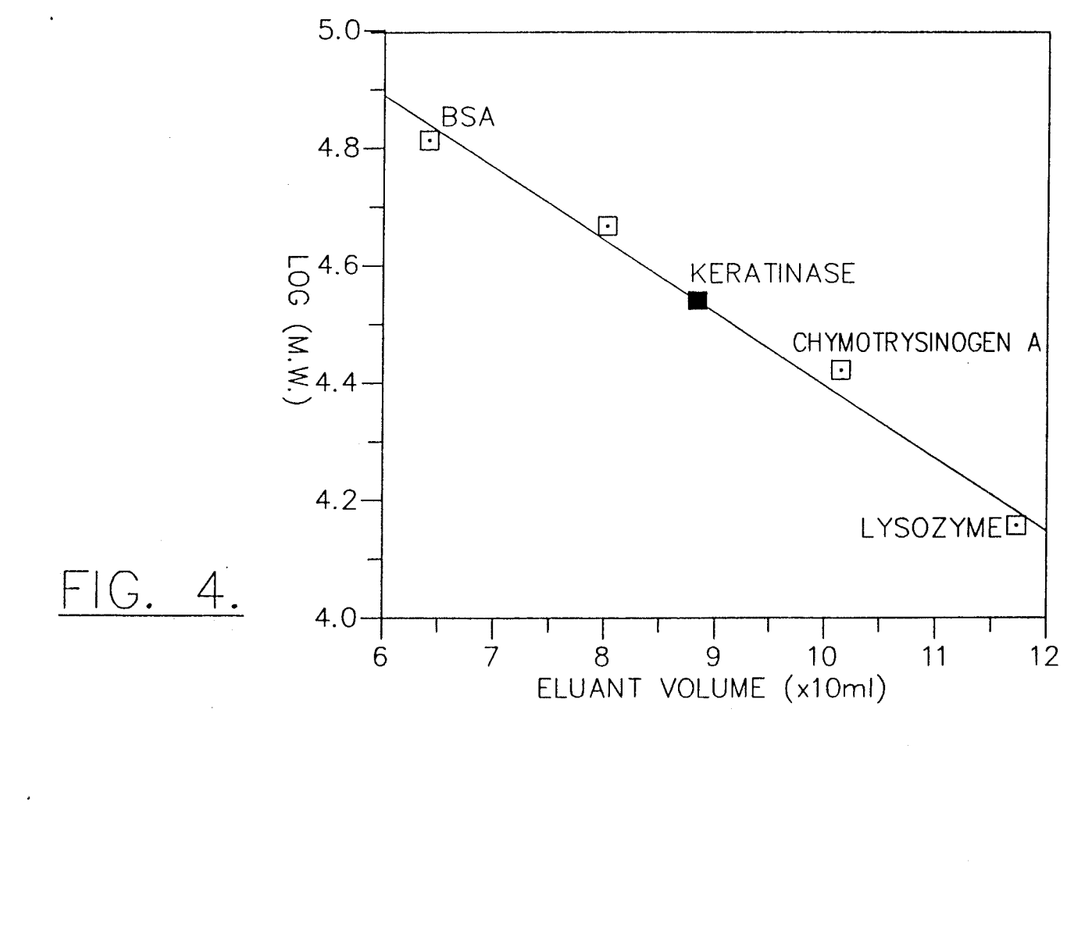
FIG. 4 shows a graph plotting molecular weight versus eluant volume for keratinase and the molecular weight standards used in gel filtration.

FIG. 3 shows the calibration profile of the Sephandex G-75 column. The native molecular weight was estimated a standard curve plot of log MW versus elution volume (FIG. 4). The results indicate an estimated native molecular weight of 33 kDa for the purified keratinase.

(ii) SDS-polyacrylamide gel electrophoresis (SDS-PAGE). To examine further the subunit molecular weight of the keratinase, discontinuous SDS-polyacrylamide gel electrophoresis was used as described by Laemmlli, Cleavage of structural proteins during the assembly of the head of bacteriophage Tg, 277 Nature 680 (1970). The gel (16 cm×20 cm×1.5 cm) consisted of a 12% polyacrylamide separating gel and a 4% polyacrylamide stacking gel. Sample preparation began with precipitation of the protein from a 0.5 ml aliquot of purified keratinase by adding 55 $\mu$l of 50% TCA and 5 $\mu$l of sodium deoxycholate (1 mg/ml). After mixing, the sample was placed in an ice bath for at least 30 min. The precipitate was pelleted by centrifugation at 14,800 ×g for 5 min. The supernatant was removed and the pellet washed with 0.5 ml of ethyl ether. After centrifuging again, the pellet was dried in vacuo for at least 10 min. The pellet was dissolved in 25 $\mu$l of 0.125 M tris-HCl buffer, pH 6.8 and 25 $\mu$l of 2X sample buffer (20% glycerol and 4% bromphenol blue) was added. Electrophoresis was started at a current of 20 mA. The amount was increased to 60 mA when tracking dye entered the separating gel and held at 60 mA until the tracking dye reached the far edge of the gel. The protein bands were brought into view with 0.1% solution of Coomassie Brilliant Blue R-250.

Figure 5:
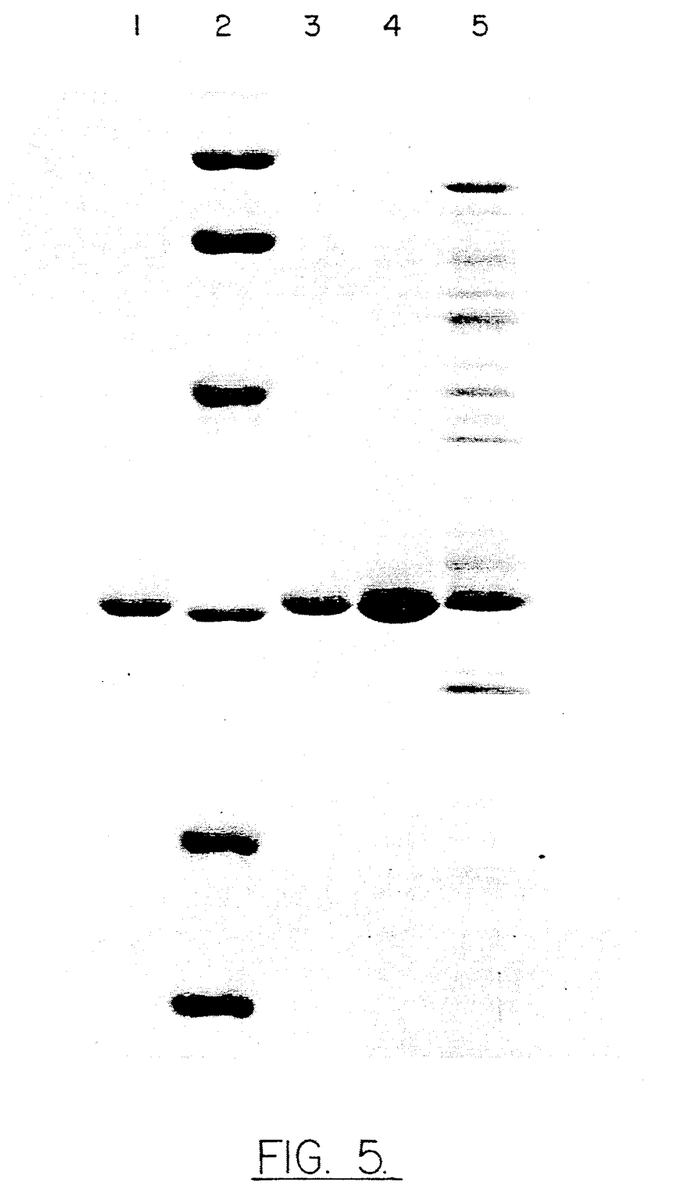
FIG. 5 shows the results of SDS-polyacrylamide gel electrophoresis of purified keratinase. Lanes 1 and 3 are purified keratinase. Lane 2 is a mixture of molecular weight standards. Lane 4 is CM-cellulose treated enzyme preparation. Lane 5 is a crude enzyme preparation.
Figure 6:
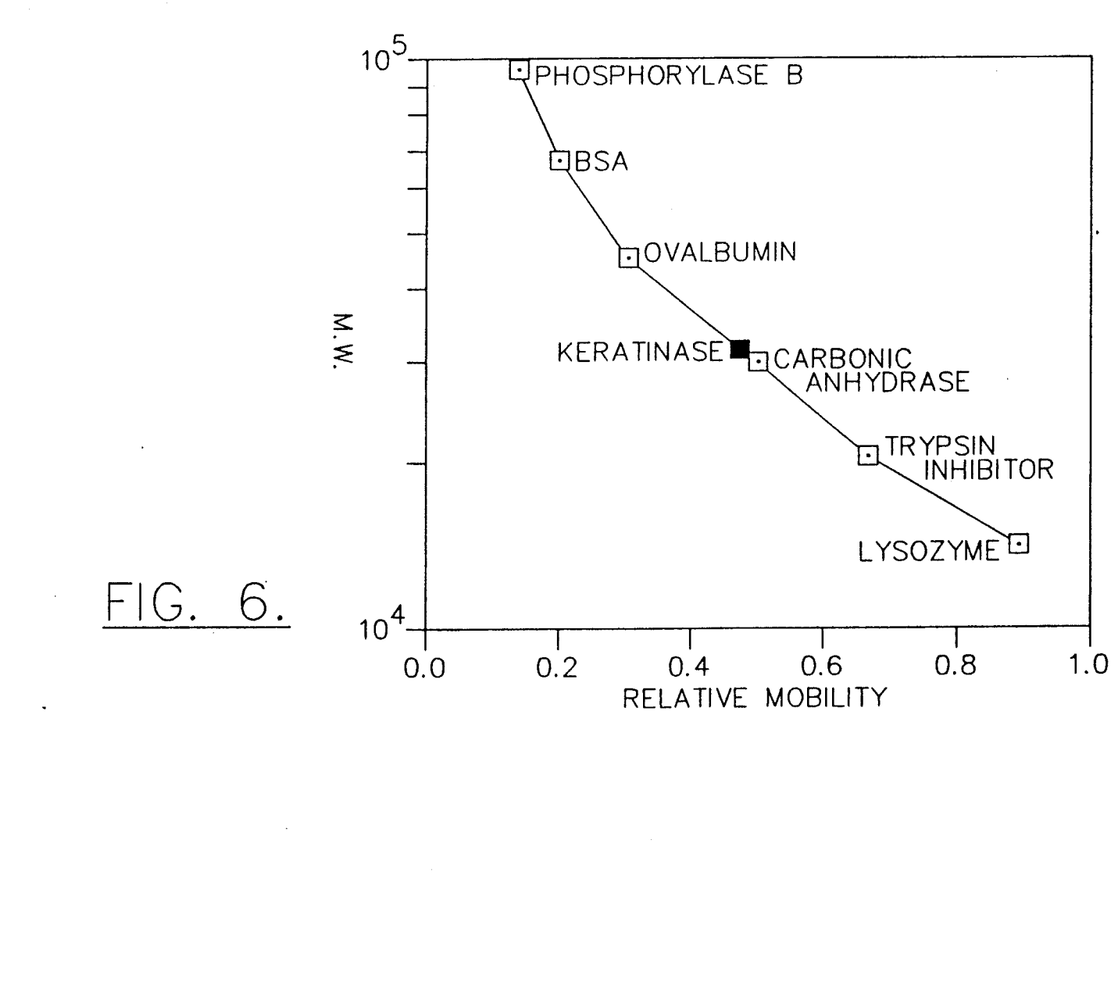
FIG. 6 shows a graph plotting molecular weight versus mobility in electrophoresis gel for keratinase and molecular weight standards.

The results from the SDS-PAGE closely mirror the results obtained from gel filtration. FIG. 5 shows the gel itself. Lanes 1 and 3 represent the purified enzyme, while Lane 2 represents the compounds used as molecular weight standards. FIG. 6 shows a plot of the molecular weight standards and keratinase as a function of mobility in the gel. The keratinase band migrated to a point which indicates its molecular weight to be 33 kDa. The fact that this value coincides with that found by gel filtration suggests that the keratinase molecules has no subunits.

Isoelectric Point Determination

Isoelectric focusing, as described by the Bio-Rad Instruction Manual (Bio-Rad, Richmond, Calif. 94804, U.S.A., catalog #161-0310), was used to determine the isoelectric point of the keratinase. A LKB horizontal electrophoresis unit (LKB 2117 multiphor) was used to make the evaluation. LKB Ampholines were used to generate a pH gradient in polyacrylamide gel. IEF standard markers were obtained from Bio-Rad. The protein bands were stained using the Bio-Rad Silver Stain Kit according to the method as developed by Mehta & Patrick, Detection of oligoclonal bands in unconcentrated CSF: Isoelectric focusing and silver staining. 33 Neurology 1365 (1983); Confavreux et al, Silver stain after isoelectric-focusing of unconcentrated cerebrospinal-fluid-Visualization of total protein and direct immunofixation of immunoglobulin G, 3 Electrophoresis 206 (1982).

Figure 7:
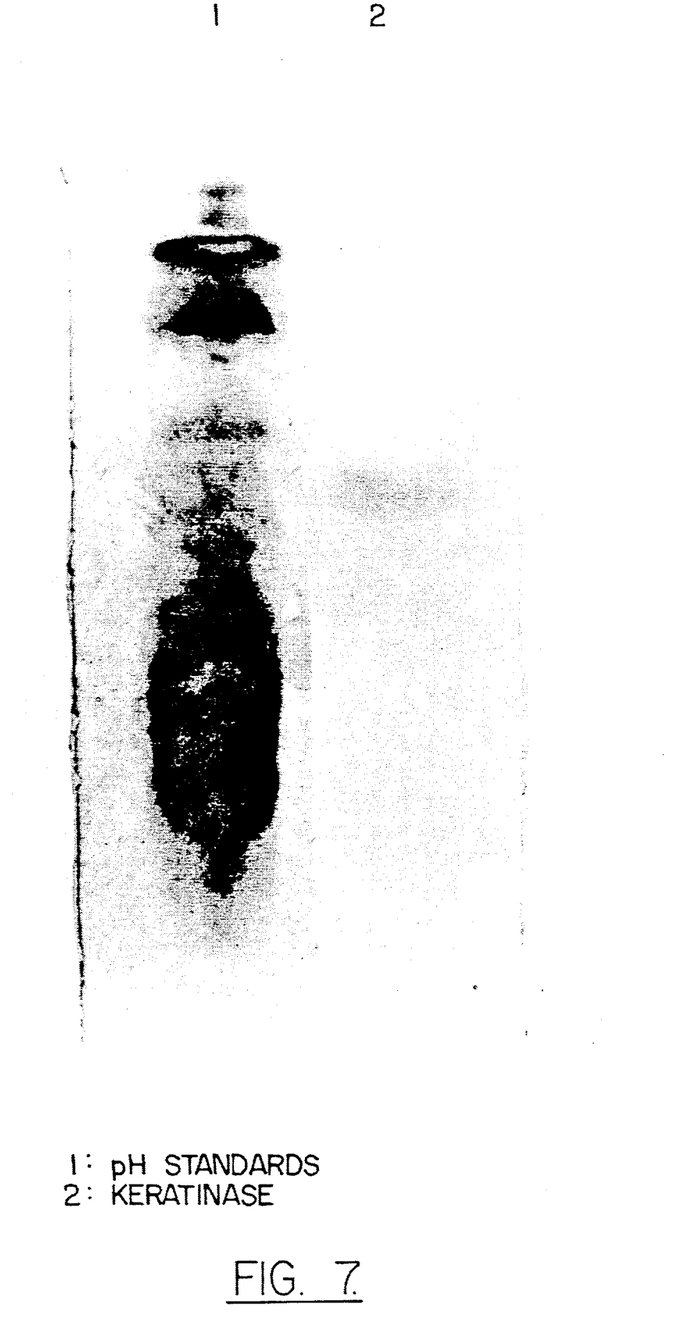
FIG. 7 shows the results of the determination of the isoelectric point of keratinase through the use of isoelectric focusing gel.

After comparing the keratinase band within the gel with the standard IEF bands, the isoelectric point (pI) was determined to be 7.25 (FIG. 7).

Determination of Enzyme Optimum pH and Optimum Temperature

The optimum pH and temperature for keratinase activity were determined utilizing the azo-keratin hydrolysis test described above. A series of 50 mM potassium phosphate buffers were prepared with pH values ranging from 5.05 to 9.22. The azo-keratin digestion test was performed as described above but the pH of the phosphate buffer was varied. To determine the optimum temperature, the azo-keratin digestion test was performed at temperatures ranging from 30°-70° C. with the pH held constant at 7.5.

Figure 8:
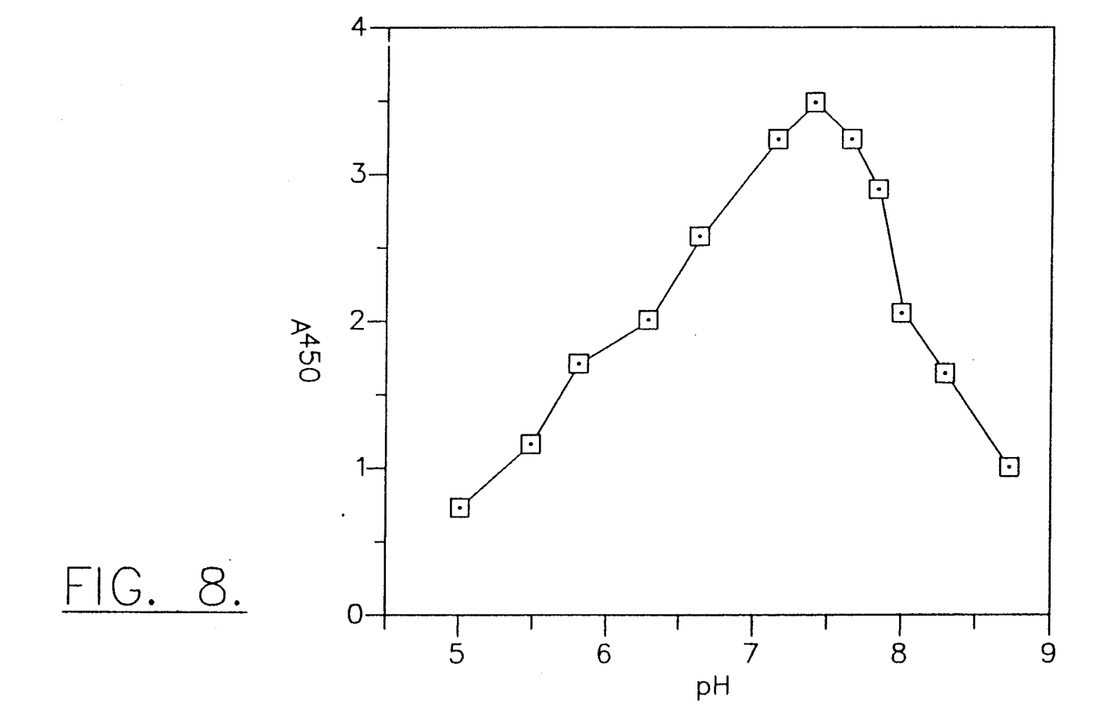
FIG. 8 shows the results of the determination of the optimum pH for keratinase activity.
Figure 9:
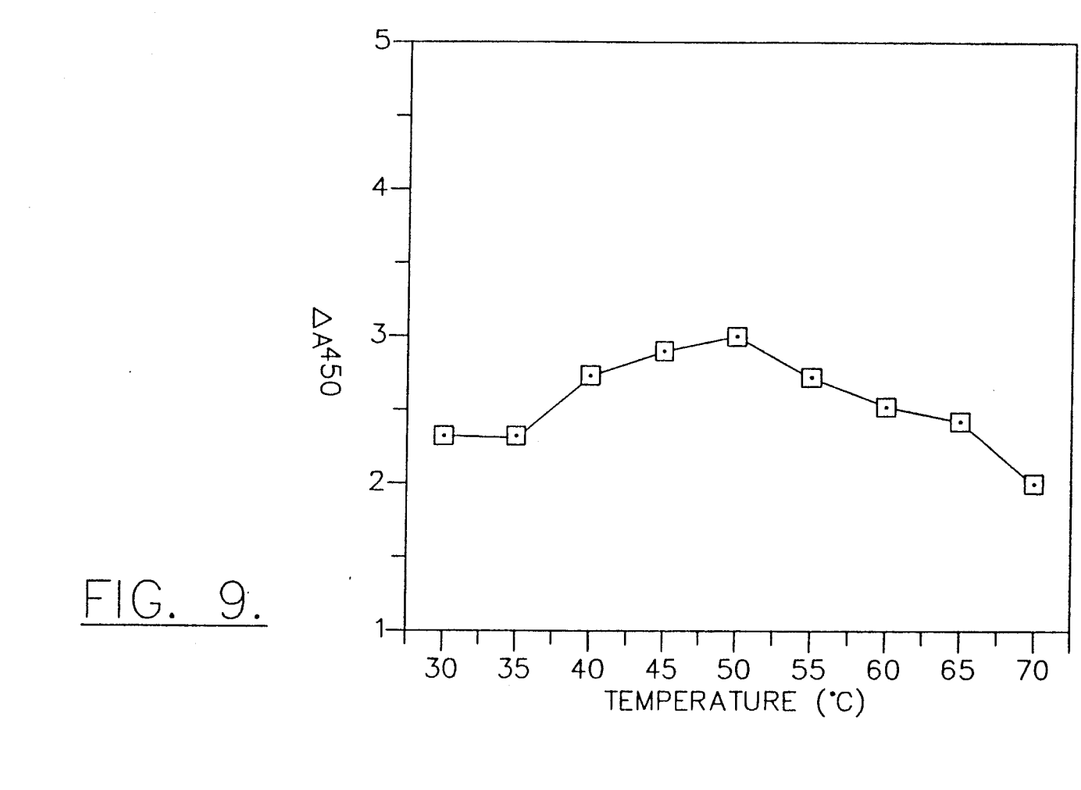
FIG. 9 shows the results of the determination of the optimum temperature for keratinase activity.

The results indicate that the pH for optimum keratinase activity is 7.5 (FIG. 8). The optimum temperature was determined to be 45°-50° C. (FIG. 9).

Thermal Stability

Aliquots (30 $\mu$g/ml) of a keratinase sample were stored at three different temperatures (−20° C., 4° C. and 25° C.). After 8 and 13 days the keratinase activity of each of the aliquots was assayed by the azo-keratin hydrolysis test and compared to the activity of keratinase before storage. SDS-polyacrylamide gel electrophoresis was performed to examine the loss of enzyme after 19-day incubations.

After 8 days of incubation, the keratinase held at −20° C. had lost only 2% of its activity; that held at 4° C. sustained a 10% activity loss. However, after 8 days the activity of keratinase held at 25° C. declined more than 90% (See FIG. 9). The activity loss continued after 13 days to 4% at −20° C., 16% at 4° C. and almost 96% at 25° C. Finally, after 19 days, keratinase held at −20° C. lost 7% of its activity, that held at 4° C. lost 22%, and that held at 25° C. showed a complete loss of activity.

Figure 10:
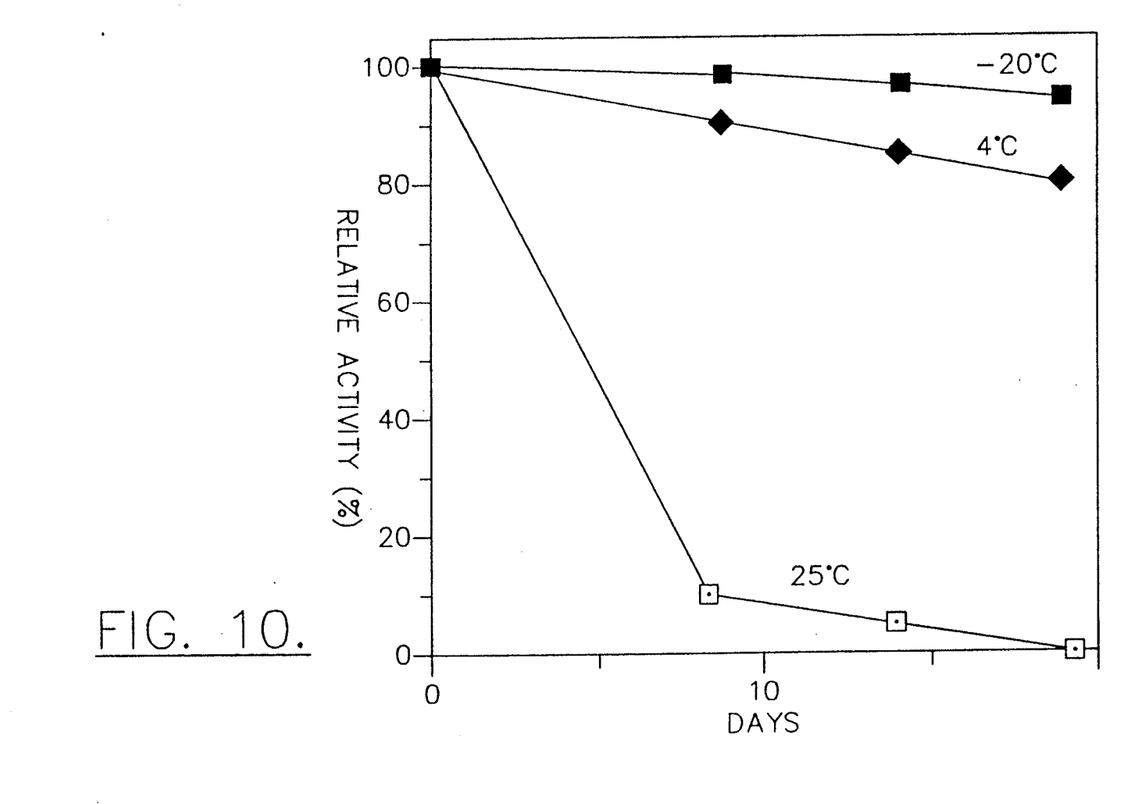
FIG. 10 shows the thermal stability of keratinase over time through a plot of keratinolytic activity versus time at different temperatures.
Figure 11:
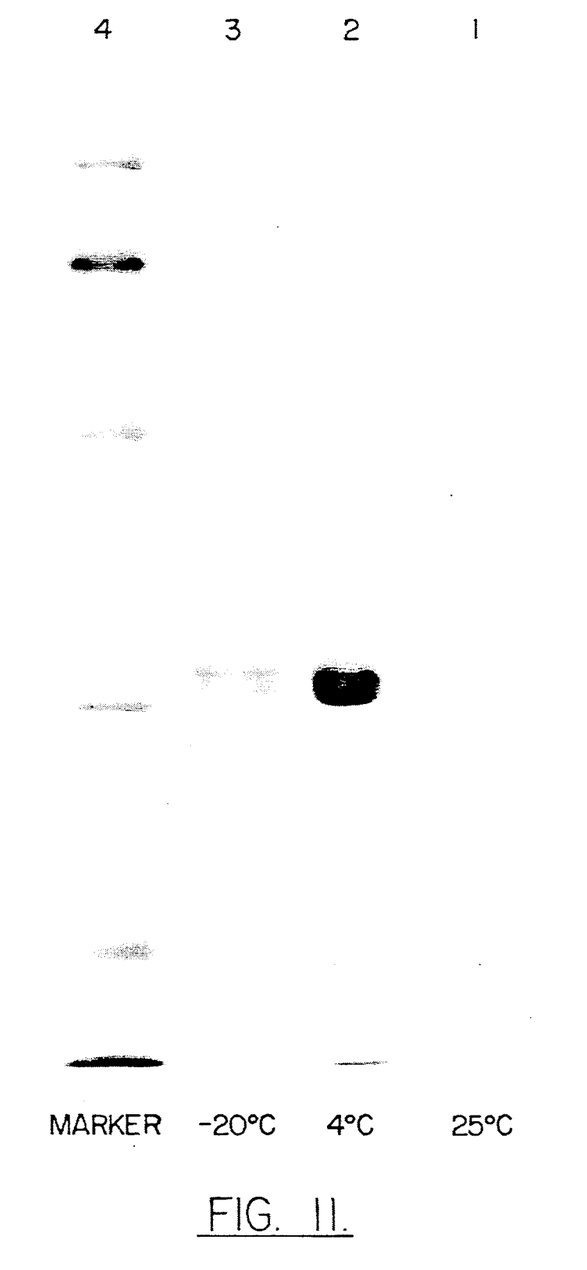
FIG. 11 shows the results of SDS-PAGE performed on keratinase incubated for 19 days at different temperatures. Lane 1 represents keratinase held at 25° C., lane 2 shows keratinase held at 4° C., lane 3 shows keratinase at −20° C., and lane 4 represents molecular weight markers.

FIG. 10 shows the electrophoresis gel produced after 19 days of incubation. Examination of lane 4, which contains the sample from 25° C., shows that the keratinase band has nearly disappeared. Lane 2, containing the 4° C. incubation, shows that the keratinase band has lightened and that two additional bands have appeared. After incubation at −20° C., the band in lane 3 is still very dark and is virtually identical to a band without thermal storage. (see FIG. 11).

The foregoing examples are provided to illustrate the present invention, and are not to be taken as restrictive thereof. The scope of the invention is defined by the following claims, with equivalents of the claims to be included therein.

That which is claimed is:

1. A substantially pure *Bacillus licheniformis* PWD-1 keratinase.

* * * * *